(12) United States Patent
Zeng et al.

(10) Patent No.: US 10,517,641 B2
(45) Date of Patent: Dec. 31, 2019

(54) ANTI-FRACTURE SHEATH AND DELIVERY SYSTEM HAVING SAME

(71) Applicant: Venus Medtech (Hangzhou), Inc., Hangzhou, Zhejiang (CN)

(72) Inventors: Min Zeng, Hangzhou (CN); Zhifei Zhang, Hangzhou (CN)

(73) Assignee: Venus Medtech (Hangzhou) Inc, Hangzhou (CN)

( * ) Notice: Subject to any disclaimer, the term of this patent is extended or adjusted under 35 U.S.C. 154(b) by 170 days.

(21) Appl. No.: 15/396,716

(22) Filed: Jan. 2, 2017

(65) Prior Publication Data
US 2017/0202576 A1    Jul. 20, 2017

Related U.S. Application Data

(63) Continuation of application No. PCT/CN2015/078877, filed on May 13, 2015.

(30) Foreign Application Priority Data

Jul. 3, 2014  (CN) .......................... 2014 1 0315347

(51) Int. Cl.
*A61B 17/34* (2006.01)
*A61M 39/08* (2006.01)
(Continued)

(52) U.S. Cl.
CPC ....... *A61B 17/3468* (2013.01); *A61M 25/005* (2013.01); *A61M 25/0074* (2013.01);
(Continued)

(58) Field of Classification Search
CPC ............ A61M 25/005; A61M 25/0052; A61M 2025/0024; A61M 39/08;
(Continued)

(56) References Cited

U.S. PATENT DOCUMENTS

| 6,544,215 B1 | 4/2003 | Bencini et al. |
| 2002/0038140 A1* | 3/2002 | Yang ...................... A61F 2/958 623/1.12 |

(Continued)

FOREIGN PATENT DOCUMENTS

| CN | 103431926 A | 12/2013 |
| CN | 103446655 A | 12/2013 |

(Continued)

OTHER PUBLICATIONS

International Search Report for PCT/CN2015/078877.
Office Action dated Feb. 1, 2016 for corresponding China Application No. 20140315347.5.

*Primary Examiner* — Shaun L David
*Assistant Examiner* — Brigid K Byrd
(74) *Attorney, Agent, or Firm* — Raymond Sun

(57) ABSTRACT

The present invention provides an anti-fracture sheath. The anti-fracture sheath comprises a tube body and an expansion section for accommodating an implantable device, wherein one side of the distal end of the tube body is joined with the expansion section, at least two reinforcing ribs are axially arranged on the tube wall of the expansion section in an internally extending manner, and the proximal ends of the reinforcing ribs extend from the expansion section and are fixedly connected with the tube wall of the tube body; and the materials of the reinforcing ribs are Kevlar fibers, the diameter of each reinforcing rib is from 0.03 mm to 0.12 mm, and the number of the reinforcing ribs is from two to four. The anti-fracture sheath provided by the present invention has the advantage that the strength of the expansion section is improved when the whole compliance of the sheath is maintained, thereby avoiding fracture of the sheath in an implantable device releasing process.

13 Claims, 2 Drawing Sheets

(51) Int. Cl.
*A61M 25/00* (2006.01)
*A61B 17/00* (2006.01)

(52) U.S. Cl.
CPC ... *A61M 39/08* (2013.01); *A61B 2017/00243* (2013.01); *A61M 25/0052* (2013.01); *A61M 2025/0024* (2013.01)

(58) Field of Classification Search
CPC ...... A61M 2025/0059; A61M 25/0144; A61M 2025/0063; A61M 25/0051–0053; A61M 25/0074; A61B 17/3468
See application file for complete search history.

(56) References Cited

U.S. PATENT DOCUMENTS

| | | | | |
|---|---|---|---|---|
| 2002/0183781 | A1* | 12/2002 | Casey | A61B 17/22031 606/198 |
| 2003/0004493 | A1* | 1/2003 | Casey | A61M 25/005 604/525 |
| 2006/0264907 | A1* | 11/2006 | Eskridge | A61M 25/0023 604/528 |
| 2006/0287669 | A1* | 12/2006 | Casey | A61B 17/22031 606/200 |
| 2009/0163946 | A1* | 6/2009 | Casey | A61B 17/22031 606/200 |
| 2009/0171348 | A1* | 7/2009 | Guo | A61M 25/0052 606/41 |
| 2012/0277729 | A1* | 11/2012 | Melsheimer | A61M 25/005 604/525 |
| 2013/0006174 | A1* | 1/2013 | Phan | A61L 29/06 604/96.01 |
| 2013/0338677 | A1* | 12/2013 | Schwitzer | A61F 2/0095 606/108 |
| 2014/0228814 | A1* | 8/2014 | Zhou | A61M 25/0043 604/528 |

FOREIGN PATENT DOCUMENTS

| | | |
|---|---|---|
| CN | 104069582 A | 10/2014 |
| CN | 204017106 U | 12/2014 |

* cited by examiner

ANTI-FRACTURE SHEATH AND DELIVERY SYSTEM HAVING SAME

TECHNICAL FIELD

The present invention belongs to the technical field of medical apparatuses, and in particular relates to an anti-fracture sheath with improved strength and a delivery system having the anti-fracture sheath.

BACKGROUND

Interventional surgery causes small traumas to the human body and has a low invasion degree, which is a medical technology rapidly developed and popularized in recent years. Generally, with the help of an interventional medical sheath (such as a delivery sheath, a guide sheath and the like), a channel is established between a lesion site in the body of a patient and operating end of the outside, and is used for guiding a medical device, medicines, an device and the like to the lesion site. The interventional medical sheath has a proximal end and a distal end, the distal end can enter the vessel system of the human body after loading therapeutic medicines and devices, and the proximal end is connected with the operating handle. In use, a wire guiding track is generally pre-established, the distal end of the sheath or the distal end communicated with another auxiliary device punctures through and enters the vessel, and by utilizing the operating handle, the doctor controls the distal end of the sheath to move to the site along the pre-established wire guiding track, withdraws the sheath, and then releases the medicines, the device, and the like.

In consideration of the intricate characteristic of the vessel system of the human body and remote operations, the sheath generally should have sufficient axial force and excellent compliance. Before reaching the lesion site, due to the compliance of the sheath, the distal end of the sheath can adaptively adjust to a bending direction to comply with the vessels of the body when the distal end of the sheath advances along the wire guiding track under the pushing action applied by the doctor.

For example, the Chinese patent with the publication number of CN103446655A discloses an adjustable bent sheath and a delivery system having the same. The adjustable sheath comprises a tube body, the tube body has a distal end and a proximal end, reinforcing and traction wires are axially arranged in the tube wall of the tube body, the distal end of the traction wire is fixed at the distal end of the tube body, and the proximal end of the traction wire extends from the tube body and is connected with an operating handle. The adjustable bent further comprises an expansion section communicated with the tube body, and the expansion section is connected with one side of the distal end of the tube body and is used for accommodating an implantable device (such as a shape memory alloy stent and the like).

In such technology, in order to improve the connection strength between the expansion section and the tube body, the expansion section and the tube body are connected by using a thickened transition section, thereby solving the problem of connection strength between the expansion section and the tube body.

However, in order to ensure the compliance of the expansion section to a maximum extent after the expansion section loads a device, in most cases, the expansion section is a pure plastic sheath without adding a net-shaped reinforcing layer capable of influencing the compliance and the diameter, and the expansion section still is a part with the weak tensile property in the whole sheath.

Technical Problems

The present invention provides an anti-fracture sheath, which can improve the tensile strength of the expansion section while keeping the integral compliance of the sheath, thereby avoiding risks generated when the sheath is fractured in an implantable device releasing process under an ectopia condition.

SUMMARY

Technical Solution

An anti-fracture sheath comprises a tube body and an expansion section for accommodating an implantable device, the distal end of the tube body is joined with the expansion section, at least two reinforcing ribs are axially arranged on the tube wall of the expansion section in an internally extending manner, and the proximal ends of the reinforcing extend from the expansion section and are fixedly connected with the tube wall of the tube The proximal ends and the distal ends of the tube body and the reinforcing ribs correspond to an operating end of the outside, the proximal ends are relatively closer to the operating end of the outside, and the distal ends are relatively further to the operating end of the outside.

During an implantation procedure, in order to ensure the compliance of the expansion section, in most cases, the expansion section still utilizes a pure plastic sheath without adding a net-shaped reinforcing layer capable of influencing the compliance and the diameter, and at this time, due to the individual difference of the human bodies, if a delivery sheath experiences a bend, the thinner expansion section loading the device is easiest to be bent. Additionally, because angiography images depending on X-rays, ultrasonic waves and the like during the implantation operation are two-dimensional images, the doctor may experience judgment errors corresponding to such bending state due to the difference of clinical experience, and if the does not immediately judge the bending state and still forcibly withdraws the sheath to release implantable device, the expansion section will partially bear a strong tensile force and can be easily fractured. In the prior art, if no additional reinforcing components are arranged in the expansion section, the expansion section can only bear the tensile force of about 20 KG, in the present invention, the reinforcing ribs are utilized to improve the strength of the section, and one end of each reinforcing rib is fixedly connected with the tube body into a whole body, so that the two added reinforcing ribs greatly share the axial large tensile force borne by expansion section; at this time, the expansion section with the added reinforcing ribs can bear tensile force of more than 50 KG, thereby preventing the expansion section from fracturing. Due the arrangement of the reinforcing ribs, when the doctor withdraws the tube body at the end by utilizing the operating handle during a clinical practice, the tensile force of more than 50 KG can effectively stop the withdrawn; step of the doctor, that is, when the doctor feels a relatively larger resistance and judges that the tube body is difficult to withdraw, the doctor the withdrawal steps and re-adjusts the sheath, thereby preventing a dangerous situation that the doctor forcedly releases the stretched expansion section to cause the expansion section to be fractured when the doctor experiences clinical judgment errors due to the limited tensile resistance of the expansion section and the complexity of the individual case.

The material selection of the reinforcing ribs is very important. The tube body and the expansion section are generally made of plastic (such as PE) materials, and the reinforcing ribs are embedded in the expansion section in a forming process for the expansion section, so that materials of the reinforcing ribs and the material of the expansion section should have great compatibility, and the reinforcing ribs and the expansion section are unlikely to layer or crack after welding.

Preferably, the reinforcing ribs are made from macromolecular materials. The macromolecular materials have relatively great compatibility with the material of the expansion section and also have excellent flexibility.

In the macromolecular materials, fibers have better strength and flexibility, so, further preferably, the reinforcing ribs are fibers. A single fiber at least can bear the tensile force of 15 KG, and in order to ensure excellent compatibility between the fiber and the expansion the surface of the fiber should have sufficient roughness in order to improve the connection strength of a contact surface between the fiber and the expansion section.

When the reinforcing ribs and the expansion section are welded, the heating is generally controlled to be higher about 5 degrees centigrade than the temperature of the material of the expansion section, and the inciting point of the fiber is further higher than the melting point of the material of the expansion section, so that the interior structure of the fiber does not generate huge changes due to the rise in temperature at the heating temperature during welding, and the fiber can still maintain excellent strength and flexibility.

Further preferably, the materials of the reinforcing ribs are Kevlar fibers.

The Kevlar fibers (poly (p-phenylene terephthalamide) fibers) have the advantages of good tensile resistance, light weight, good flexibility and the like, and are widely applied to the industrial and military fields, such as body armors, traction cables and the like. The Kevlar not only have relatively greater compatibility with the PE materials of the expansion section, also can be firmly connected with the tube body, thereby preventing a problem that the significance of the reinforcing ribs is already lost even if the expansion section is not fractured due to the fact that the reinforcing ribs separate from the tube body when the tensile force is too large.

The reinforcing ribs and the expansion section have excellent connection strength, so that deformation of the reinforcing ribs and the expansion section under the tensile force basically synchronously changes. The reinforcing ribs have higher tensile property, so that the deformation of the reinforcing ribs is small and is at least smaller than fracture elongation of the expansion section when the whole sheath bears a relatively larger tensile force, thereby avoiding the fracture of the expansion section.

The expansion section needs relatively greater flexibility, so, preferably, the expansion section does not have a reinforcing layer. The expansion section is only made of pure plastic materials, and the thickness of the wall is small and generally is 0.4 mm, so the reinforcing ribs should have a smaller diameter in order to be embedded into the tube wall of the expansion section, but if the diameter is too small, the strength of the expansion section will be seriously reduced, preferably, the diameter of each reinforcing rib is from 0.03 mm to 0.12 mm, and further preferably from 0.05 mm to 0.1 mm. The section shape of each reinforcing rib is not strictly limited, and conventionally available reinforcing ribs can be utilized; the section shape of each reinforcing rib may be circular or flat (such as an ellipse with large difference between the of a real axis and the length of an imaginary axis, or a rectangle with large difference between length and the width); the reinforcing ribs need to be embedded into the tube all of the expansion section, so that the thickness (namely the length vertical to the tube wall direction) of each reinforcing rib cannot be too large due to the limitation of the tube wall of the expansion section; and when the thickness is the same, a flat reinforcing rib has a larger section area, ensuring that the reinforcing ribs have higher strength.

The number and arrangement of the reinforcing ribs also have relatively larger to the integral mechanical property of the sheath. Preferably, the number of the reinforcing is from two to four, further preferably two. If the number of the reinforcing ribs is too large, flexibility of the sheath is reduced. Meanwhile, the trend and arrangement form of each reinforcing rib also halve a certain requirement, and each reinforcing rib extends in the axial direction of the expansion section, that is, the reinforcing ribs are parallel with each other. Further preferably, the reinforcing ribs are uniformly distributed along the circumference of the expansion section. Therefore, the force application points of the expansion section can be relatively uniformly distributed, and excessive centralization of the partial stress is avoided.

The reinforcing ribs are mainly used for preventing the expansion section from breaking, so that the reinforcing ribs should be located at the radial central position of the expansion section.

During manufacturing, one side of the distal end of the tube body and the expansion section mutually surround each other and then are welded together. In order to further improve connection strength, the proximal ends of the reinforcing ribs extend from the expansion section, that is, after the expansion section is manufactured, a part of the reinforcing ribs is not in the tube wall of the expansion section, and when the expansion section and the tube body are butt-joint and welded, the part, extending from the expansion section, of the reinforcing ribs are integrally welded with the tube body.

Preferably, the length of the part, extending from the expansion section and fixedly connected with the tube body, of each reinforcing rib is from 0.5 cm to 5 cm. Sufficient extension length ensures that the reinforcing ribs and the tube body are firmly combined and are unlikely to separate, thereby preventing the reinforcing ribs from being pulled out of the tube body under stress.

The part of the expansion section that is close to the tube body is easy to fracture, so end, departing from the tube body, of each reinforcing rib does not strictly need to extend to the end head of the expansion section, preferably, the length each reinforcing rib in the expansion section is smaller than or equal to the length of the expansion section. Meanwhile, in order to ensure that the length of each reinforcing rib is sufficient and each reinforcing rib can extend to the entire easy-to-fracture part, the extension length of each reinforcing rib in the axial direction of the expansion section is at least one third of the length of the expansion section.

The present invention further provides a delivery system. The delivery system comprises the anti-fracture sheath, a sheath core located in the anti-fracture sheath and an operating handle fixed with the proximal ends of the anti-fracture sheath and the sheath core.

The sheath core comprises a core tube, a guide head and an implantable device fixing head are fixed at the distal end of the core tube, a part, located between the guide head and the implantable device fixing head, of the core tube is a mounting section for accommodating an implantable device, and the expansion section is located on the periphery of the mounting section and wraps the implantable device.

Beneficial Effects of the Present Invention

Compared with the prior art, the anti-fracture sheath provided by the present invention has the advantage that the strength of the expansion section is improved when the integral compliance of the sheath is maintained, thereby avoiding the fracture of the sheath in an implantable device releasing process.

DESCRIPTION OF THE EMBODIMENTS

The following further illustrates the present invention in conjunction with specific embodiments.

Figure 1:
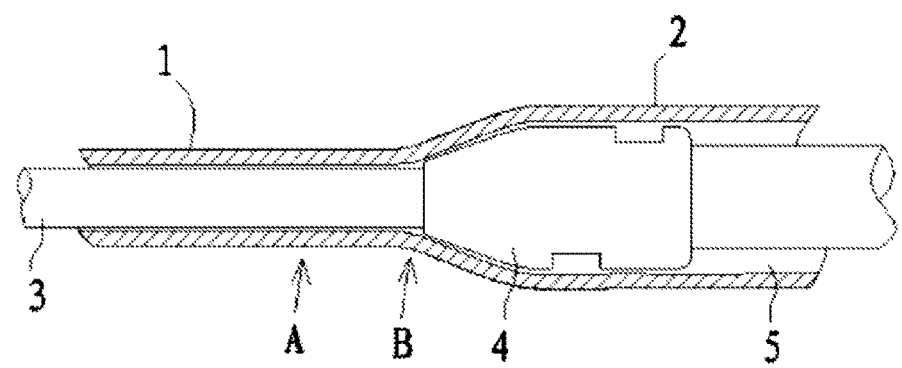
FIG. 1 is a structural schematic diagram of a sheath and a sheath core in the prior art only describes a connection part of an expansion section and a tube body.

FIG. 1 is a structural schematic diagram of a sheath and a sheath core in the prior art, and only describes a connection part of an expansion section and a tube body.

As shown in FIG. 1, the sheath comprises a tube body 1 and ab expansion section 2 that communicates with the distal end of the tube body 1. A channel in the sheath is used for allowing extension of a sheath core therethrough, the sheath core comprising a core tube 3, a fixing head 4 and a guide head (not shown in FIG. 1) fixed at the end part of the distal end of the core tube, and an accommodating chamber 5 is formed between an inner wall of the expansion section 2 and a part between the fixing head 4 and the guide head and is used for accommodating an implantable device. In the present invention, the sheath core from the prior art can be utilized.

The expansion section 2 is a tubular structure, the diameter of which is slightly larger than that of the tube body 1. In an interventional surgical procedure, the interior of the expansion section 2 can accommodate and compress the implantable device, and ensures that the implantable device is released after the implantable device moves to an implantation site in a compressed state. The expansion section should have a certain radial elastic force and axial stretching resistance, and meanwhile, the inner wall of the expansion section should be as smooth as possible in order to conveniently release and recover the implantable device.

During machining, a prefabricated expansion section and a tube body mutually surround, a surrounding transition section is approximately located between a point A and a point B in FIG. 1, and the strength of the surrounding transition section can be improved in a thickening manner.

In the interventional surgical procedure, after the distal end of the sheath reaches the implantation site, the sheath starts releasing the implantable device; that is, the sheath core remains stationary, the sheath is withdrawn, and then the implantable device is gradually released. If the implantable device is made from a shape memory alloy material, it will recover its set shape under the effect of body temperature during release, thereby achieving predetermined functions.

However, the interior structure of the human body is complex. When the implantable device reaches a lesion site, the whole expansion section may experience a large bend. Sometimes, the expansion section may assume a bent condition as shown in FIG. 2, and a part C is stacked or twisted; if the sheath is withdrawn to release the implantable device at this time, the withdrawal resistance of the sheath is gradually increased, and obviously, if the bent expansion section continues to bear the withdrawing tensile force, a part D will be a section under the maximum withdrawing tensile force; and during the interventional surgical procedure, a doctor observes the states of the devices through X-rays or ultrasonic two-dimensional images, and if the doctor lacks experience to delay the judgment and continues withdrawing the sheath under the withdrawing resistance, the tensile force borne by the part D of the expansion part is centralized and is sharply increased.

Figure 2:
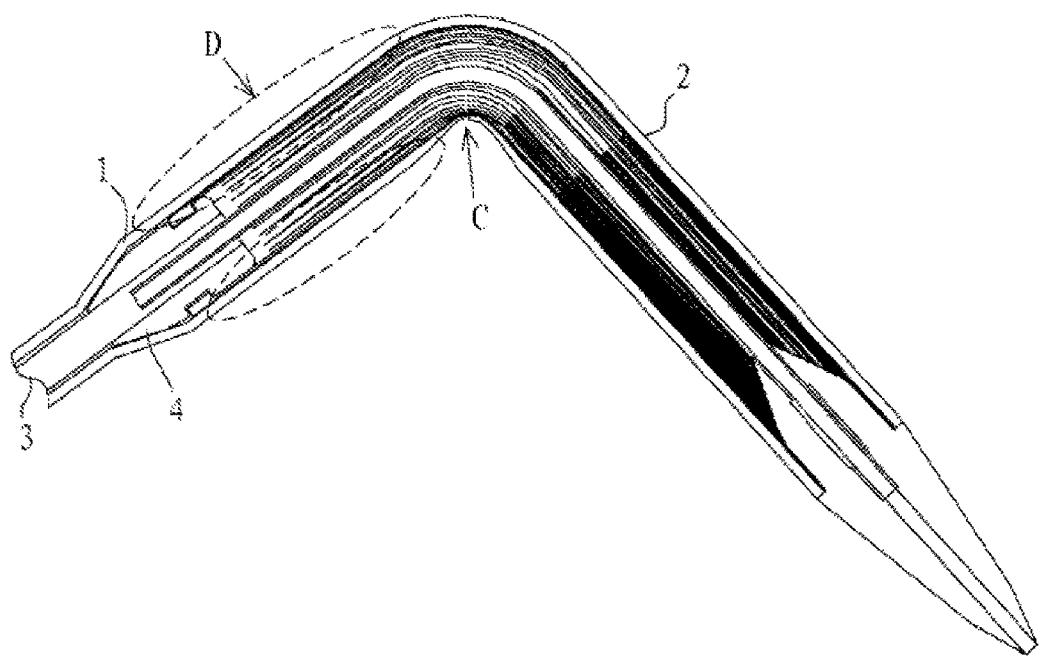
FIG. 2 is a schematic diagram of the sheath in FIG. 1 under a bending condition.
Figure 3:
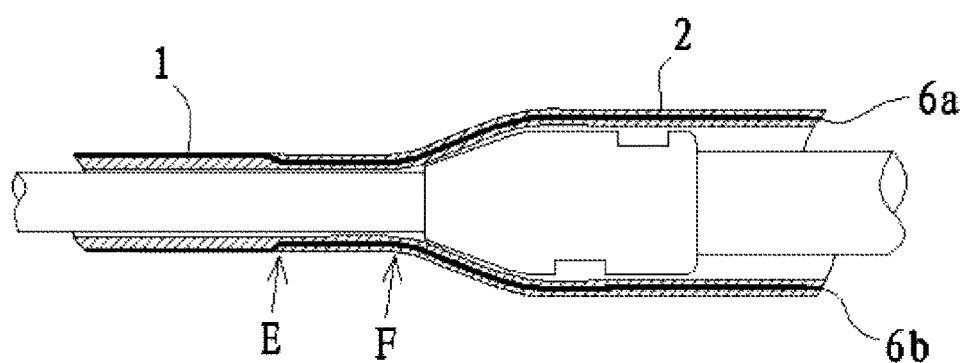
FIG. 3 is a structural schematic diagram of an anti-fracture sheath provided by the present invention and only describes a connection part of an expansion section and a tube body.

If bent, the part C grips the implantable device, so that it is difficult for the tensile force to reach the right side of the part C in FIG. 2; the part D is the weakest part from the left side of the part C to the proximal end of the sheath in FIG. 2, so that the part D is most prone to fracture if the tensile force is too large, resulting in a huge clinical risk for the interventional surgical procedure. Referring to FIG. 3, an anti-fracture sheath provided by an embodiment of the present invention comprises a tube body 1 and an expansion section 2 for accommodating the implantable device.

The tube body 1 can utilize the tube body from the prior art, for example, the tube body can sequentially comprise an inner layer and an outer layer from interior to exterior. The inner layer and the outer layer can be made from the same or different macromolecular lubricating materials, for example, the inner layer can be made from a polytetrafluoroethylene material, and the outer layer can be made from a polyethylene material. According to strength requirements, a reinforcing layer can be arranged between the inner layer and the outer layer, and the reinforcing layer has a bourdon tube structure knitted by steel wires. Due to the bourdon tube structure, the sheath not only has a certain axial supporting force, hut also has a good bending flexibility, and the tube body also has better radial flexibility.

Two reinforcing ribs are arranged in the tube all of the expansion section 2 and respectively are a reinforcing rib 6a and a reinforcing rib 6b. In FIG. 3, the surrounding pan of the tube body 1 and the expansion section 2 is located between a point E and a point F, proximal ends of the two reinforcing ribs extend from the expansion section 2, namely extending over the point E, and the extending sections of the two reinforcing ribs are Welded in the tube all of the tube body 1.

In this embodiment, the tube body 1 (the outer layer) and the expansion section 2 are made from a polyethylene material. The reinforcing ribs are embedded in the expansion section 2 during formation of the expansion section 2, the materials of the reinforcing ribs are Kevlar fibers (poly (p-phenylene terephthalamide) fibers), and such fiber has the advantages of good tensile property, light weight, flexibility and the like, and also has relatively greater compatibility with the expansion section made from the polyethylene material.

The expansion section 2 needs relatively greater flexibility, so that the thickness of the wall of the expansion section 2 is relatively smaller, generally 0.4 mm, and on this basis, the diameter of each reinforcing rib is 0.05 mm. In order to ensure the flexibility, the expansion section 2 does not utilize other reinforcing components except for the reinforcing ribs, which is totally different from the prior art, thereby avoiding the use of a metal structure or a complex net-shaped reinforcement structure.

Figure 4:
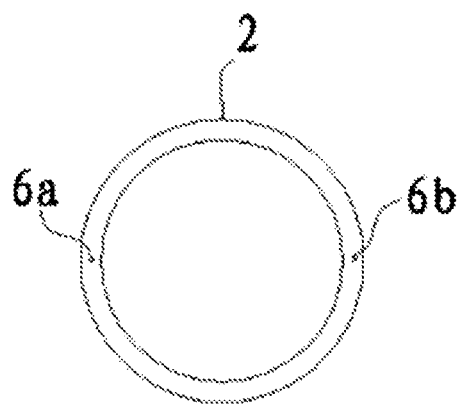
FIG. 4 is a schematic diagram of sectional positions of reinforcing ribs in an expansion section of the present invention.

By combining with FIG. 4, in the embodiment, the reinforcing rib 6a and the reinforcing rib 6b are located in the tube wall of the expansion section 2, and each reinforcing rib extends along the longitudinal direction of the expansion section. The reinforcing rib 6a and the reinforcing rib 6b are symmetrically distributed in the two side walls of the expansion section 2, so that force application points for stretching the expansion section 2 are distributed relatively uniformly, and excessive centralization of local stress is avoided.

During manufacturing, after one side of the distal end of the tube body 1 mutually surrounds the expansion section 2, the reinforcing rib 6a and the reinforcing rib 6b extend 3 cm from the expansion section 2 (over the point E in FIG. 3), the extending sections are positioned on the outer all of the tube body 1, parts, located between the point F and the point F, of the tube body 1 and the expansion section 2 are welded, and meanwhile, the two reinforcing ribs positioned on the outer wall of the tube body 1 are also welded on the outer wall of the tube body 1.

In FIG. 3, the right side of the point F is the weak part. In this embodiment, one end of each reinforcing rib away from the tube body 1 extends to an axial central part of the expansion section 2, that is, the extending length of each reinforcing rib is half of the length of the expansion section.

In use, even if the sheath is bent, the sheath can bear the tensile force of more than 50 KG due to addition of the reinforcing ribs to the part D in FIG. 2. During clinical practice, when withdrawing the tube body at the proximal end by utilizing an operation handle, the doctor feels a relatively larger resistance and judges that it is difficult to withdraw the tube body, and then the doctor stops the withdrawal step; and at this time, deformation of the reinforcing ribs under the tensile force is much smaller than the deformation needed to fracture the expansion section, so that the expansion section is not fractured under this tensile force, and the doctor can re-adjust the sheath to avoid the fracture of the expansion section.

Figure 5:
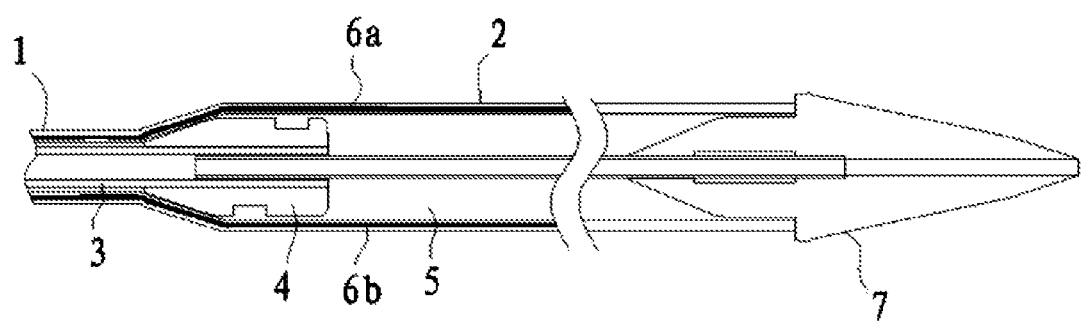
FIG. 5 is a schematic diagram of an internal structure of a distal end part of a delivery system in the present invention.

Referring to FIG. 5, the embodiment further provides a delivery system comprising the anti-fracture sheath, the sheath core located in the anti-fracture sheath and an operation handle fixed with the proximal ends of the anti-fracture sheath and the sheath core.

The sheath core comprises a core tube 3, the distal end of the core tube 3 is fixed with a guide head 7 and a fixing head 4, and a part, located between the guide head 7 and the fixing head 4, of the core tube 3 is a mounting section for accommodating the implantable device.

The sheath tube comprises a tube body 1 and an expansion section 2 that communicates with one side of the distal end of the tube body 1, and an accommodating chamber 5 is formed between the mounting, section and the inner Wall of the expansion section 2 and is used for accommodating the implantable device.

In this embodiment, two reinforcing, ribs are arranged in the anti-fracture sheath in order to improve the strength of the expansion section. Based on tests, the expansion section can bear the tensile force of more than 50 KG after the two reinforcing ribs are arranged in the sheath. In clinical practice, when the doctor withdraws the tube body at the proximal end by utilizing the operation handle, and if the connection part of the expansion section and the tube body experiences a large bend, the doctor feels the relatively larger resistance and judges that it is difficult to withdraw the sheath tube, so the doctor stops the withdrawal step, and re-adjusts the sheath to avoid the fracture of the expansion section.

What is claimed is:

1. An anti-fracture sheath which has a side wall defining a lumen and having a radial outer surface and a radial inner surface, the sheath longitudinally comprising:
    an expansion section configured to accommodate an implantable device within the lumen, and
    a tube body connected with the expansion section;
    wherein the sheath further comprises at least two reinforcing ribs arranged between the radial outer surface and the radial inner surface of the side wall, and each of the reinforcing ribs extends along a longitudinal direction of the sheath and comprises a first section and a second section along its length and a bend transitioning between the first section and the second section when the sheath is in a straight configuration, wherein the first section is located farther from the radial inner surface of the side wall than the second section.

2. The anti-fracture sheath according to claim 1, wherein the first section is positioned at the radial outer surface of the side wall.

3. The anti-fracture sheath according to claim 1, wherein the first section is welded at the radial outer surface of the side wall.

4. The anti-fracture sheath according to claim 1, wherein the reinforcing ribs are made from macromolecular materials.

5. The anti-fracture sheath according to claim 4, wherein the reinforcing ribs are fibers.

6. The anti-fracture sheath according to claim 5, wherein the materials of the reinforcing ribs are Kevlar fibers.

7. The anti-fracture sheath according to claim 1, wherein the expansion section is devoid of a reinforcing layer.

8. The anti-fracture sheath according to claim 1, wherein the second section has a portion located at the expansion section, and the length of the portion is smaller than or equal to the length of the expansion section.

9. The anti-fracture sheath according to claim 8, wherein the length of the portion of the second section is half of the length of the expansion section.

10. The anti-fracture sheath according to claim 1, wherein the length of the first section is from 3 cm to 5 cm.

11. The anti-fracture sheath according to claim 1, wherein the number of the reinforcing ribs is from two to four.

12. The anti-fracture sheath according to claim 1, wherein the diameter of each reinforcing rib is from 0.03 mm to 0.12 mm.

13. A delivery system, comprising the anti-fracture sheath according to claim 1, a sheath core located in the anti-fracture sheath, and an operation handle fixedly connected with a proximal end of the anti-fracture sheath and a proximal end of the sheath core.

* * * * *